(12) United States Patent
Draper et al.

(10) Patent No.: US 10,898,684 B2
(45) Date of Patent: Jan. 26, 2021

(54) NON-BUCKLING STEERABLE CATHETER

(71) Applicant: Sanovas Intellectual Property, LLC, Reno, NV (US)

(72) Inventors: Jeffrey Draper, San Francisco, CA (US); Roy E. Morgan, Alameda, CA (US)

(73) Assignee: Sanovas Intellectual Property, LLC, Reno, NV (US)

( * ) Notice: Subject to any disclaimer, the term of this patent is extended or adjusted under 35 U.S.C. 154(b) by 150 days.

(21) Appl. No.: 15/714,341

(22) Filed: Sep. 25, 2017

(65) Prior Publication Data

US 2018/0085557 A1 Mar. 29, 2018

Related U.S. Application Data

(60) Provisional application No. 62/398,896, filed on Sep. 23, 2016.

(51) Int. Cl.
*A61M 25/01* (2006.01)
*A61B 1/00* (2006.01)
(Continued)

(52) U.S. Cl.
CPC ....... *A61M 25/0147* (2013.01); *A61B 1/0057* (2013.01); *A61B 1/00078* (2013.01); *A61B 1/00147* (2013.01); *A61M 25/0054* (2013.01); *A61M 25/10* (2013.01); *A61B 17/7074* (2013.01); *A61B 2017/00323* (2013.01);
(Continued)

(58) Field of Classification Search
CPC .......... A61M 25/0147; A61M 25/0136; A61M 25/0144; A61M 25/0012; A61M 25/01; A61M 25/005; A61M 25/0133; A61M 25/0141; A61M 25/0054
See application file for complete search history.

(56) References Cited

U.S. PATENT DOCUMENTS 5,171,305 A * 12/1992 Schickling ......... A61M 25/0119
604/271
5,190,050 A * 3/1993 Nitzsche ........... A61M 25/0136
600/585
(Continued)

FOREIGN PATENT DOCUMENTS

EP 2135634 B1 * 10/2011 ........ A61M 25/0147
WO WO-2018022404 A1 * 2/2018 ........ A61M 25/0141

*Primary Examiner* — Nathan R Price
*Assistant Examiner* — Mark A Igel
(74) *Attorney, Agent, or Firm* — Forge IP, PLLC (57) ABSTRACT

A steerable member is disclosed generally having a steerable member for a medical apparatus, including a continuous, elongated body having a proximal section, a distal section, and a middle section between the proximal and distal sections, where the proximal section of the elongated body is less flexible than the distal section. At least one pull wire sheath extends through the proximal section and the middle section, but not through the distal section, and has a channel therethrough. A pull wire is disposed in the channel of the sheath and extends through the proximal section, middle section and distal section of the elongated body, the pull wire having a distal end affixed to a distal end of the elongated body, so that the distal section of the elongated body bends in response to a force applied to the proximal end of the pull wire.

20 Claims, 4 Drawing Sheets

(51) Int. Cl.
  *A61B 1/005* (2006.01)
  *A61M 25/00* (2006.01)
  *A61M 25/10* (2013.01)
  *A61B 17/70* (2006.01)
  *A61F 2/44* (2006.01)
  *A61F 2/48* (2006.01)
  *A61B 17/00* (2006.01)
  *A61F 2/50* (2006.01)

(52) U.S. Cl.
  CPC ............ *A61F 2/442* (2013.01); *A61F 2002/48* (2013.01); *A61F 2002/5093* (2013.01)

(56) References Cited

U.S. PATENT DOCUMENTS

| | | | | |
|---|---|---|---|---|
| 5,304,198 A * | 4/1994 | Samson | ............ | A61M 25/0045 600/585 |
| 5,318,525 A * | 6/1994 | West | ............ | A61B 18/1492 600/585 |
| 5,383,852 A * | 1/1995 | Stevens-Wright | ............ | A61M 25/0136 604/95.04 |
| 5,383,923 A * | 1/1995 | Webster, Jr. | ............ | A61B 5/0422 607/125 |
| 5,399,164 A * | 3/1995 | Snoke | ............ | A61M 25/01 604/264 |
| 5,487,757 A * | 1/1996 | Truckai | ............ | A61B 18/1492 604/264 |
| 5,702,433 A * | 12/1997 | Taylor | ............ | A61M 25/0144 604/22 |
| 5,715,817 A * | 2/1998 | Stevens-Wright | ............ | A61B 18/1492 600/373 |
| 5,720,719 A * | 2/1998 | Edwards | ............ | A61B 10/0233 604/22 |
| 5,916,214 A * | 6/1999 | Cosio | ............ | A61M 25/0144 600/374 |
| 6,120,499 A * | 9/2000 | Dickens | ............ | A61B 18/1492 600/374 |
| 6,551,302 B1 * | 4/2003 | Rosinko | ............ | A61M 25/0084 604/22 |
| 2001/0037084 A1 * | 11/2001 | Nardeo | ............ | A61M 25/0138 604/95.04 |
| 2002/0165461 A1 * | 11/2002 | Hayzelden | ............ | A61M 25/0138 600/523 |
| 2002/0165534 A1 * | 11/2002 | Hayzelden | ............ | A61M 25/0144 606/41 |
| 2005/0131279 A1 * | 6/2005 | Boulais | ............ | A61B 1/0052 600/141 |
| 2005/0273006 A1 * | 12/2005 | Stewart | ............ | A61B 18/1492 600/433 |
| 2006/0252993 A1 * | 11/2006 | Freed | ............ | A61M 25/0147 600/146 |
| 2010/0168666 A1 * | 7/2010 | Tegg | ............ | A61M 25/0147 604/95.04 |
| 2010/0280320 A1 * | 11/2010 | Alvarez | ............ | A61B 17/00234 600/146 |
| 2010/0280449 A1 * | 11/2010 | Alvarez | ............ | A61B 34/30 604/95.04 |
| 2010/0280525 A1 * | 11/2010 | Alvarez | ............ | A61B 34/30 606/130 |
| 2011/0270229 A1 * | 11/2011 | Tanaka | ............ | A61B 1/0057 604/528 |
| 2012/0203169 A1 * | 8/2012 | Tegg | ............ | A61M 25/0136 604/95.04 |
| 2012/0277671 A1 * | 11/2012 | Fuentes | ............ | A61M 25/005 604/95.04 |
| 2014/0275770 A1 * | 9/2014 | Gunday | ............ | A61B 1/0684 600/104 |
| 2014/0275777 A1 * | 9/2014 | Gunday | ............ | A61F 7/123 600/109 |
| 2015/0283356 A1 * | 10/2015 | Kanemasa | ............ | A61M 25/0012 604/526 |
| 2015/0352327 A1 * | 12/2015 | Helgeson | ............ | A61M 25/0147 604/95.04 |
| 2016/0096004 A1 * | 4/2016 | Gerrans | ............ | A61B 1/045 600/112 |

\* cited by examiner

NON-BUCKLING STEERABLE CATHETER

FIELD OF THE INVENTION

The present invention relates to systems and methods for moving a medical apparatus, such as a catheter or endoscope, in bodily cavities. More specifically, the present invention relates to a steerable member having a construction that permits the distal tip to be articulated by pull wires while preventing the member from buckling.

BACKGROUND OF THE INVENTION

In general, catheters are used in medical procedures in which tubular structures, lumens, pleural cavities or spaces of the body, such as airways, vessels, organs, and joints are diagnostically examined and/or therapeutically treated. Catheters, which can be introduced into the body through a natural orifice or through an incision, can deliver imaging devices, surgical instruments, implants, fluids, drugs, pharmacologic materials, biologic materials, biologic agents and therapeutics to treat or remedy various pathologies found therein. Catheters also guide and deliver other components, such as guide wires, scaffolds, stents, and tools to the intended site within the body.

Endoscopes/imaging catheters are widely used in medicine to provide direct visualization for diagnostic and therapeutic purposes. They are available in many sizes and configurations intended for use in different parts of the body and for a variety of diagnostic and therapeutic procedures. The visualization device (i.e., a fiber optic image bundle or a sensor at the distal tip of the device), together with a means of illumination, are an integral part of the endoscope. Endoscopes may also provide working channels to guide and deliver other instruments to the desired site.

Steerable catheters are common in the medical device world. They often function by embedding a wire into a secondary lumen of a polymer extrusion, which deflects the distal tip of the extrusion when pulled. A major problem of steerable catheters is that, while the distal tip steers, the proximal section buckles under the compression force of the wires being pulled. An additional problem is that, when the steerable catheter is bent, the wires are put in tension and the distal tip will curve. This buckling is significantly mitigated, but not completely eliminated, when the wires are nested inside the lumens of steel coil tubes embedded in the walls of the extrusion.

This buckling of the catheter takes away from the precision in which the tip is steered, and it significantly limits the catheter's functionality when used in confined spaces. Moreover, the buckling of the catheter exerts significant lateral forces on sensitive and often diseased anatomy, and these lateral forces can injure that anatomy.

What is desired, therefore, is a steerable member for catheters and the like that does not buckle when force is exerted on the pull wires to steer it. What is further desired is steerable that is able to be steered with precision and accurately maneuverable in small spaces.

SUMMARY OF THE INVENTION

Accordingly, it is an object of the present invention to provide a steerable member with a construction that eliminates buckling of the catheter body.

It is a further object of the present invention to provide a steerable member with a construction that optimizes insertion of a catheter.

It is yet another object of the present invention to provide a steerable member with a construction that optimizes translation characteristics that comport with specific anatomic segments.

In order to overcome the deficiencies of the prior art and to achieve at least some of the objects and advantages listed, the invention comprises a steerable member for a medical apparatus, including a continuous, elongated body having a proximal section, a distal section, and a middle section between the proximal and distal sections, wherein the proximal section of the elongated body is less flexible than the distal section, at least one pull wire sheath extending through the proximal section and the middle section but not extending through the distal section, the pull wire sheath having a channel therethrough, and a pull wire disposed in the channel of the sheath and extending through the proximal section, middle section and distal section of the elongated body, the pull wire having a distal end affixed to a distal end of the elongated body, wherein the distal section of the elongated body bends in response to a force applied to the proximal end of the pull wire.

In some embodiments, the middle section of the elongated body has an inner diameter smaller than the inner diameter of the proximal section, such that the pull wire sheath penetrates a wall of the elongated body where it passes into the middle section.

In certain embodiments, the distal section of the elongated body comprises a polymer with a lower durometer than the proximal section. In some of these embodiments, the distal section of the elongated body comprises a polymer with a lower durometer than the middle section, in some, the middle section of the elongated body comprises a polymer with a lower durometer than the proximal section, and in some, the middle section of the elongated body comprises a polymer with a lower durometer than the proximal section and a higher durometer than the distal section.

In certain advantageous embodiments, the proximal section of the elongated body further comprises a ribbon braid, and the middle section does not include the ribbon braid. In some of those embodiments, the ribbon braid comprises a stainless steel braid.

In some embodiments, the at least one sheath comprises a plurality of sheaths, each sheath having a pull wire disposed in the channel thereof.

In certain embodiments, the sheath comprises a coil tube, and in some cases, the coil tube comprises a stainless steel coil. In other embodiments, the sheath comprises a stainless steel ribbon braid.

In advantageous embodiments, the relationship between the elastic moduli of the distal section of the elongated body and the pull wire sheath is $$E_{polymer} \times 10^4 < E_{sheath}$$

In some cases, the invention further includes a stainless steel ring mounted in the wall of the body, wherein the pull wire is welded to the ring.

In certain embodiments, the invention includes an imaging device at the distal end of the elongated body. In some cases, the elongated body comprises the shaft of a balloon catheter, and in other cases, the elongated body comprises the shaft of an endoscope.

In another embodiment, the invention comprises a steerable member for a medical apparatus, including a continuous, elongated body, at least one pull wire sheath extending through a portion of the elongated body and having a length, the pull wire sheath having a channel therethrough and a distal end, and a pull wire disposed in the channel of the sheath and having a distal end affixed to a distal end of the elongated body, the pull wire having a length longer than the length of the sheath, wherein the elongated body has an inner diameter that reduces in size proximal to the distal end of the pull wire sheath, such that the pull wire sheath penetrates a wall of the elongated body where the diameter reduces, wherein the distal section of the elongated body bends in response to a force applied to the proximal end of the pull wire.

In some of these embodiments, the relationship between the elastic moduli of the distal section of the elongated body and the coil tube is $$E_{polymer} \times 10^4 < E_{coil}$$

DETAILED DESCRIPTION OF THE INVENTION

Figure 1A:
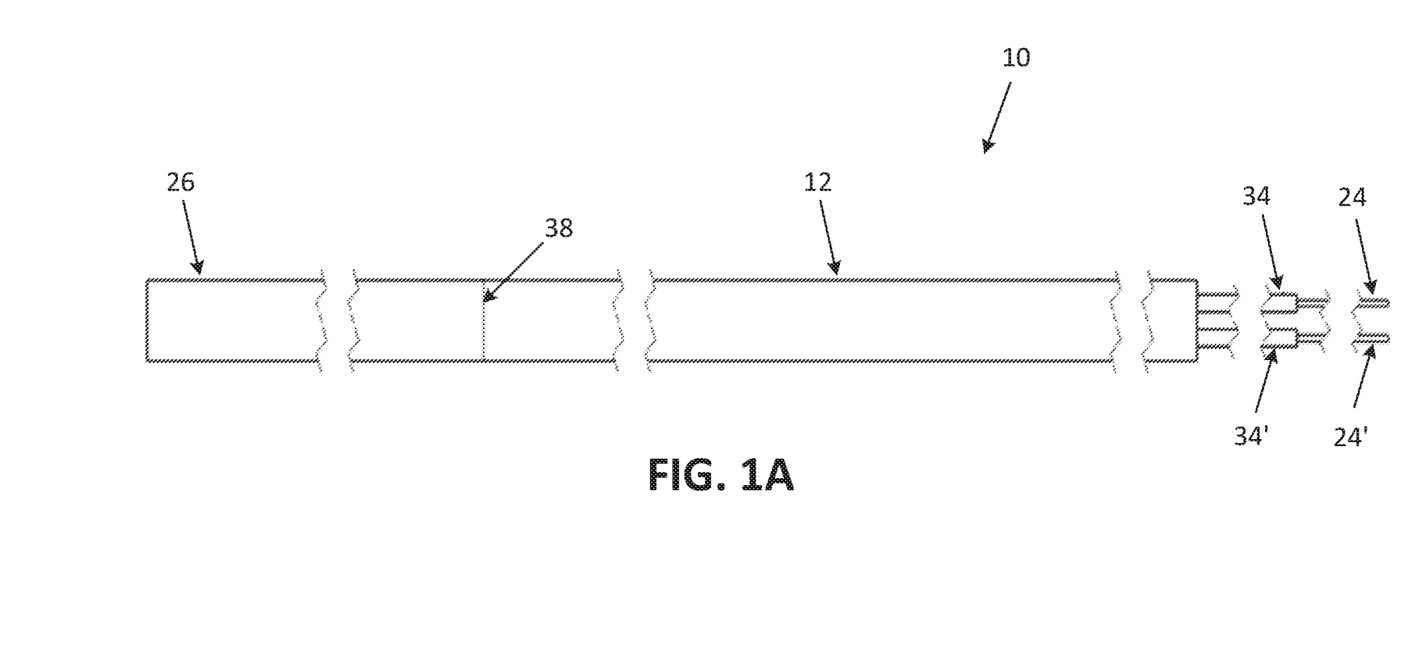
FIG. 1A is a side view of steerable member for a medical apparatus in accordance with the invention.
Figure 1B:
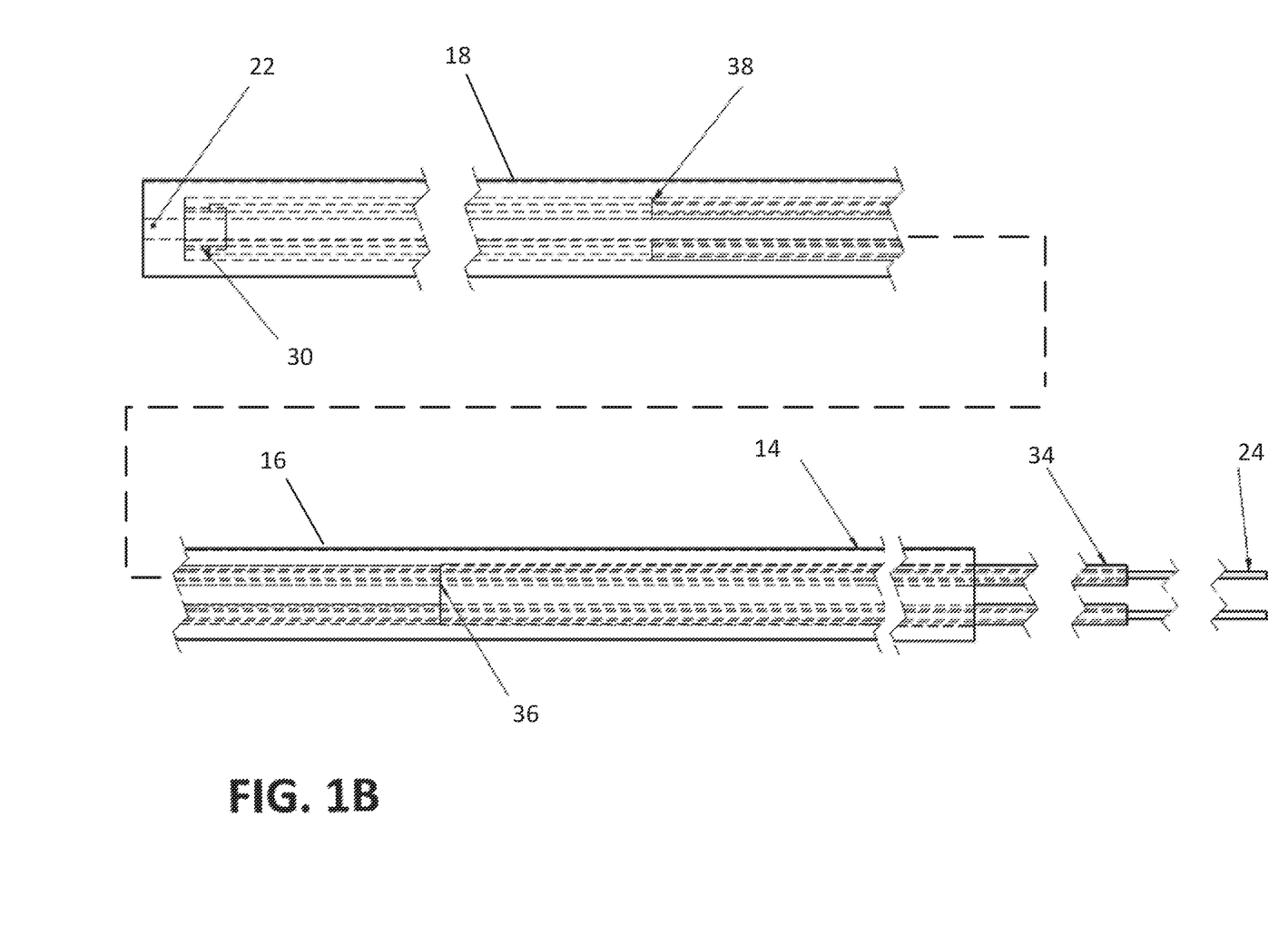
FIG. 1B is a cross-sectional side view the steerable member of FIG. 1A.

The basic components of one embodiment of a steerable member for a medical apparatus such as a catheter or endoscope in accordance with the invention are illustrated in FIGS. 1A-1B. The device comprises a continuous, contiguous, non-buckling, partially hollow member that can be used as a structural component in a variety of assemblies that would benefit from a semi-rigid to rigid body with a varying cross-sectional stiffness and an integral articulating distal component. The varying properties that form the continuously integral member provide an overall structure that can be easily navigated through tortuous luminal paths and provides steering capabilities that simplify the process. The basic construction principles of the device are described below. As used in the description, the terms "top," "bottom," "above," "below," "over," "under," "above," "beneath," "on top," "underneath," "up," "down," "upper," "lower," "front," "rear," "back," "forward" and "backward" refer to the objects referenced when in the orientation illustrated in the drawings, which orientation is not necessary for achieving the objects of the invention.

The steerable member 10 includes an elongated body 12 having a proximal section 14, a middle section 16, and a distal section 18. Any of various pliable polymers can be used to fashion the continuous elongated body 12, which is usually formed via extrusion. These sections have varied levels of stiffness or flexibility, and consequently, varied levels of resistance to bending and undesirable buckling, as is further outlined below.

A central lumen 22 is defined by an inner diameter of the body 12 that extends along the length thereof. The lumen 22 may be used for the passage of bodily fluid, such as air during respiratory procedures or blood during angioplasties. The lumen 22 may also be used to supply any of various gases and liquids for insufflating portions of the anatomy and inflating portions of medical apparatus, such as catheter balloons. The lumen could also be used to deliver diagnostic, therapeutic, and pharmaceutical agents, guidewires, other catheters, and other medical tools small enough to transit therethrough. It should be noted that the body 12 may include additional lumens for one or more of these purposes.

At least one, and typically a plurality of (e.g., two), pull wires 24, 24' extend through the proximal, middle, and distal sections 14, 16, 18, and are affixed to the distal end 26 of the body 12. In advantageous embodiments, the pull wires 24, 24' comprise steel, though in other embodiments, any material that can be formed into a fine diameter tension wire may be employed. In certain embodiments, the pull wires 24, 24' are welded to a stainless steel ring 30 mounted in the wall of the body 12.

Each pull wire 24, 24' is disposed in a support structure comprising a sheath 34, 34' surrounding the pull wire. In certain advantageous embodiments, the pull wire sheath 34 is a stainless steel coil, but in other embodiments, can be another type of coil tube, wire wrap, or other adequately rigid coil, ribbon, or similar type of sheath. The sheath 34 acts, not only as a protective outer covering for the pull wire 24, but also as a force bearing member that is in compression while the tension in the pull wire increases when it is pulled in order to cause deflection of the distal end of the catheter.

The steel coils 34, 34' extend through the proximal section 14 and middle section 16 of the body 12. At the junction of the proximal section 14 and middle section 16, the coils 34, 34' penetrate a lateral wall 36 of the extrusion, where there is a reduction in the inner diameter of body 12. The distal end 38 of the coils marks the junction of the middle section 16 and distal section 18.

The penetration point of the pull wire and coil tube assembly at wall 36 provides an advantage over traditional articulating hollow members, which have traditionally used a fully internalized wall lumen to house pull-wire members along the entire length of the extruded catheter body. A common shortcoming of these prior art systems is overcome with the understanding that force transfer from internal to external members is dependent on the relative deflection in compression of each member and its transfer point and the relative length in relation to each other.

Figure 2:
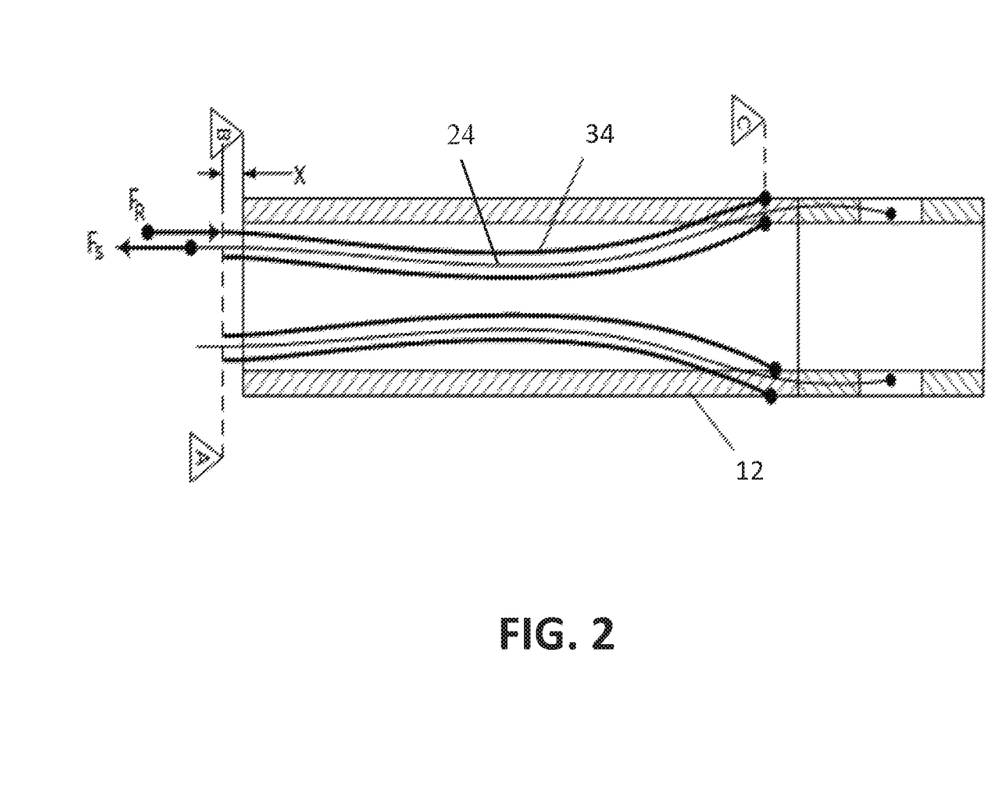
FIG. 2 is a schematic view of a steerable catheter showing the constitutive relation for the force transfer between a pull wire-sheath assembly and the outer catheter body.

For illustration, the general constitutive relation for the force transfer between the steering member and the outer extrusion is shown in FIG. 2, where the equation for the impending deflection/motion of the coil tube 34 is represented as:

$$F_s \geq F_R = \frac{\pi^2 EI}{(kL^2)} \qquad (1)$$

where: k is the Euler end condition coefficient (=2 for pinned ends)
 L is the free coil tube length
 E is Young's modulus of elasticity
 I is the area moment of inertia
and, still referring to FIG. 2, where X represents the available compression length of the coil tube 34, such that the maximum allowable deflection/motion of the coil tube 34 in order to prevent loading of the catheter body 12 is represented as:

$$\delta \leq X \qquad (2)$$

Using the relation for modulus of elasticity of the coil tube 34 as the governing member of load transfer to the external catheter body 12:

$$E = \frac{FL_O}{A_O \Delta L} \quad (3)$$

rearranged as:

$$\Delta X = \frac{F_s L_O}{A_O E} \quad (4)$$

it can be appreciated that the cross-sectional area $A_O$ and elastic modulus E govern the response of the coil tube 34, as the difference in compressed length vs. free length (L vs $L_O$) is small.

Substituting the peak buckling force above for $F_S$, it is seen that it is the moment of inertia I of the coil tube that primarily governs the deflection relation:

$$\Delta X = \frac{\left[\frac{\pi^2 EI}{(kL)^2}\right] L_O}{A_O E} = \frac{\pi^2 I}{k^2 L A_O} \quad (5)$$

It should be appreciated that sheath mechanics are more complicated than simple buckling theory predicts, due to the combination of the central wire 24 of the assembly also being in tension during the compressive loading of the sheath 34. There is a necessary sharing of buckling forces from the sheath to the pull wire at the time of sheath collapse (i.e., when the sheath exceeds its compressive strength limit). Though such conditions are rare, a description of such conditions is illustrative of the physics of this tendon-sheath system.

It is somewhat counterintuitive that a load transfer takes place between the wire and sheath at the point of compressive failure, but this is necessary in order for static-equilibrium to be maintained. If one assumes that it is possible for the tension loading of the internal pull wire to exceed the compressive ultimate strength limit of the coil sheath material, it can be appreciated that the deformation of the sheath is constrained to the path along the central axis of the pull wire under tension. It is this constraint that obviates traditional buckling theory as the appropriate description of the sheath-failure mode; a more appropriate description is that of solid-height compressive loading to failure of the sheath member.

Figure 3A:
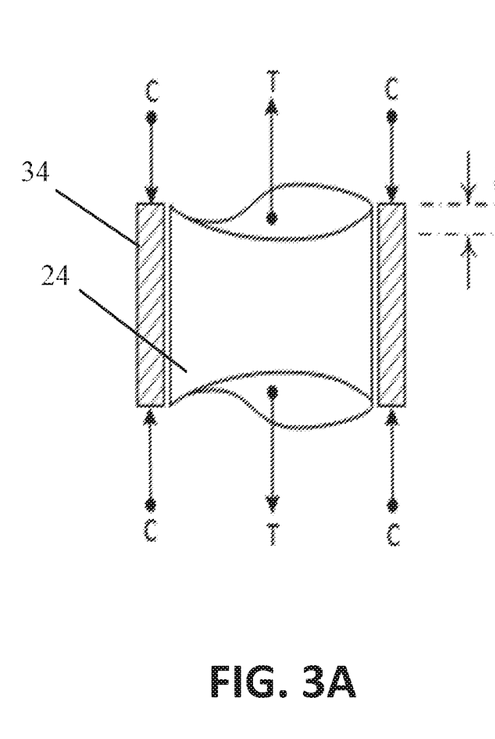
FIG. 3A is a schematic view of the differential element (dX) of a pull wire-sheath assembly.
Figure 3B:
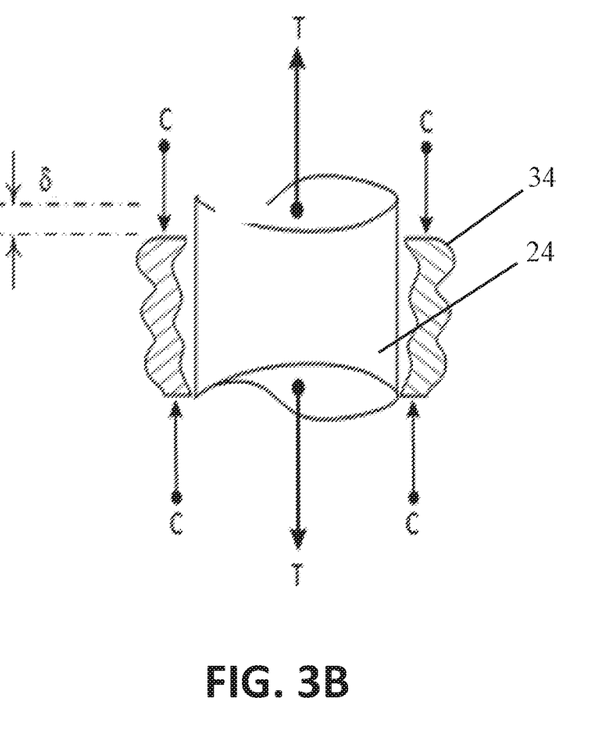
FIG. 3B is a schematic view of the differential element (dX) of a pull wire-sheath assembly in which tension has exceeded the plastic deformation limit of the sheath material.

FIGS. 3A-B illustrate the static equilibrium of a differential member of such a wire-sheath assembly that has the unique theoretical property of a wire with infinite ultimate tensile strength. Letting the end-conditions of the sheath 34 be unbound to translation, it becomes apparent that a point can be achieved where the tension force has exceeded the compressive loading of the sheath. It is only at this point, where compressive strength is exceeded, that longitudinal deformation can begin to act to shorten the net path length of the combined wire and sheath assembly.

To give some idea of the total load that a wire-sheath assembly would need to be exceeded under such conditions, one can approximate the compressive yield point for typical steel sheath, given typical steel ultimate compressive yield strength ($U_{t/cs}$) of approximately 100,000 psi, and working backward toward the force required. Assuming an internal sheath diameter of approximately 0.4 mm and outer sheath diameter of 0.6 mm, then the cross-sectional area is defined by:

$$A_{cs} = \pi(r_o^2 - r_i^2) = 0.63 \text{ mm}^2 \quad (6)$$

Because $U_{t/cs}$ is defined in units of stress (Force/Area), the force is equal to:

$$\sigma = F/A_{cs} \rightarrow A_{cs}\sigma = F \rightarrow 0.0001 \text{ in}^2 \cdot 100{,}000 \frac{\text{lb}_f}{\text{in}^2} = 100 \text{ lb}_f \quad (7)$$

This provides a sense of the typical ultimate strengths of wire forces required to cause failure of the sheath 34, which are far greater than the force required to cause deflection in the catheter body 12 itself. FIGS. 3A-B illustrate how a differential section of the wire and sheath assembly responds to the theoretical condition where wire tensile strength exceeds sheath compressive strength, and also illustrates how the sheath is constrained to collapse along the central axis of the internal pull wire.

Thus, wire pull forces below the ultimate strength of sheaths can easily be employed to effectively drive distal tip turning, typically in the domain of ~$1_{lbf}$ to $5_{lbf}$, which easily facilitates human hand manipulation of such pull wire systems for use in steering mechanisms that will not cause sheath collapse and subsequent load transfer to the external catheter body 12 due to shortening (crumpling) of the sheath 34.

As noted, various polymers can be used to fashion the continuous elongated body 12. The distal section 18 is more flexible than the proximal section 14. In certain advantageous embodiments, the distal section 18 is made with a polymer having a lower durometer than the proximal section 14. In some cases, the middle section 16 will be made of the same polymer as either the proximal section 14 or distal section 18. However, in certain embodiments, the middle section 16 has a lower durometer than the proximal section 14, and a higher durometer than the distal section 18. It should also be noted that the durometer may change within one or more of these sections 14, 16, 18, such that the elongated body 12 has a more continually changing durometer along its length, gradually getting softer with a lower durometer in the distal direction.

In certain advantageous embodiments, the proximal section 34 further includes a steel ribbon braid, providing the proximal section with further stiffness and a greater resistance to buckling. Such embodiments take advantage of the function of the combined braiding and contiguously varying material durometer configurations working in concert with the forces applied during typical pull-wire steering operations to reduce buckling tendency in such members.

In operation, the pull wire 24 is pulled by an operator's fingers during insertion of the catheter, such that the user's hand exerts a reaction force in the distal direction, while the user's thumb exerts an actuation force in the proximal direction. Due to the particular construction of the assembly, the compressive strain in distal section 18 is greater than the compressive strain in the proximal section 14, thereby causing the distal section 18 to articulate. In some embodiments, when the user actuates the pull wire 24, the compressive strain in the middle section 16 may be greater than the proximal section 14, or less than the distal section 18, or both.

In certain embodiments, the approximate relationship between the elastic moduli of the polymer of the distal section 18 and coils 34 is:

$$E_{polymer} \times 10^5 < E_{coils} \quad (7)$$

and in advantageous embodiments, is at least $$E_{polymer} \times 10^4 < E_{coils} \quad (8)$$

This relationship is important in order for the distal section 18 to compress enough to articulate without sufficient compression in the coil tubes 34 to make the catheter bend in the proximal section 14.

The aforementioned provides means for users' improved ability to navigate tortuous paths in the anatomy without reaction forces developing from buckling movement of the catheter itself when the operator attempts to turn the distal tip of the catheter. The result is a steerable catheter with no buckling of the proximal section during normal use, sealed in a polymer extrusion. This allows the catheter to be steered into small spaces and around tight corners that could not be achieved with a catheter that buckles when steered, and without the risk of liquid ingress along its length.

The invention may be used in the insertion tube for an endoscope. The proximal end of the catheter may be inserted into the handle apparatus of the endoscope and the wires attached to a disc controlled by the user's thumb. Alternatively, the wires may be attached to any similar kind of device actuation mechanism. The coil tubes could also be fixed to the handle to further control the control and/or buckling of the device. After these mechanical considerations, the endoscope can be used to observe (with a camera at the tip), take samples, or deliver treatments to various parts of the human or animal body.

Devices similar to endoscopes called boroscopes may be built using the invention, for inspecting small spaces that humans cannot directly observe with the naked eye.

Alternatively, the invention and its actuating and control mechanism(s) may be used simply as a steerable catheter and/or steerable working channel. Such an embodiment of the invention would be used to navigate a wide variety of endo luminal and airway instrumentation to target anatomy. These instruments may be incorporated into the central cannulation of the invention; functioning as a singular instrument. Alternatively, these instruments may be translated through the central cannulation of the invention; functioning as a working channel. Additionally, in another embodiment of the invention, the instrumentation may be translated along the outside of the invention; functioning as a steerable guide wire or guide sheath. These functions are not intended to be mutually exclusive. In fact, the invention can navigate a plurality of instruments at the same time with said instruments being incorporated within the central cannulation and simultaneously navigating instruments through the remaining aspect of the central cannulation, if any, and along the outside of the invention.

The invention can also be used in robotics for the purpose of deflecting the end of a flexible member from a location some distance away.

The invention can also be used in exoskeletons to connect, actuate and/or control anatomic segments and to serve as epiphyses', tendinous and ligamentous like structures. Such an embodiment can also function to enable the transmission of fluids and/or other linear control apparatus through its central cannulation and/or along its outer body.

The invention can also be used in endoskeletons to connect, actuate and/or control anatomic segments and to serve as epiphyses', tendinous and ligamentous like structures. Such an embodiment can also function to enable the transmission of fluids and/or other linear control apparatus through its central cannulation and/or along its outer body.

The invention can also be used in the repair and reconstruction of the spine as part of a spinal rodding system and/or scoliotic correction system. Such an embodiment of the invention delivers instrumentation and/or connects, stabilizes, actuates, corrects and/or controls the vertebral and/or the intervertebral bodies and/or segments of the spine.

The invention can be electronically enabled and remotely controlled via an artificially intelligent electro-mechanical, electro-pneumatic, hydraulic and/or piezo-electric control system that regulates the actuation of the pull wires. Such a system may be equipped with sensors to provide metrics, to provide feedback and/or to stimulate accentuated microcontrols to optimize the system.

It should be understood that the foregoing is illustrative and not limiting, and that obvious modifications may be made by those skilled in the art without departing from the spirit of the invention. Accordingly, reference should be made primarily to the accompanying claims, rather than the foregoing specification, to determine the scope of the invention.

What is claimed is:

1. A steerable member for a medical apparatus, comprising:
   a continuously integral elongated body having a proximal section,
   a. a distal section, a middle section, a first junction between the proximal section and the middle section, a second junction between the middle sections and the distal section, the middle section extends between the first junction and the second junction;
   wherein the proximal section of the elongated body is less flexible than the distal section;
   at least one pull wire sheath extending through the continuously integral elongated body portion, each of the at least one pull wire sheaths extending through the proximal section and the middle section but not extending through the distal section, wherein the middle section of the elongated body has an inner diameter smaller than the inner diameter of the proximal section, such that the pull wire sheath penetrates a wall of the elongated body where it passes into the middle section, each of the at least one pull wire sheaths having a channel therethrough; and
   a pull wire disposed in the channel of the sheath, the pull wire extending through the proximal section, middle section and distal section of the elongated body, the pull wire having a distal end affixed to a distal end of the elongated body;
   wherein the distal section of the elongated body bends in response to a force applied to the proximal end of the pull wire.

2. The steerable member of claim 1, wherein the middle section of the elongated body comprises a polymer section.

3. The steerable member of claim 1, wherein the distal section of the elongated body comprises a polymer with a lower durometer than the proximal section.

4. The steerable member of claim 3, wherein the polymer of the distal section has a lower durometer than the middle section.

5. The steerable member of claim 3, wherein the middle section of the elongated body comprises a second polymer with a lower durometer than the proximal section.

6. The steerable member of claim 3, wherein the middle section of the elongated body comprises a second polymer with a lower durometer than the proximal section and a higher durometer than the distal section.

7. The steerable member of claim 1, wherein the proximal section of the elongated body further comprises a ribbon braid, and the middle section does not include the ribbon braid.

8. The steerable member of claim 7, wherein the ribbon braid comprises a stainless steel braid.

9. The steerable member of claim 1, wherein the at least one sheath comprises a plurality of sheaths, each sheath having a pull wire disposed in the channel thereof.

10. The steerable member of claim 1, wherein the sheath comprises a coil tube.

11. The steerable member of claim 10, wherein the coil tube comprises a stainless steel coil.

12. The steerable member of claim 1, wherein the sheath comprises a stainless steel ribbon braid.

13. The steerable member of claim 1, wherein the relationship between the elastic moduli of the distal section of the elongated body and the pull wire sheath is $$E_{polymer} \times 10^4 < E_{sheath}.$$

14. The steerable member of claim 1, further comprising a stainless steel ring mounted in the wall of the body, wherein the pull wire is welded to the ring.

15. The steerable member of claim 1, further comprising an imaging device at the distal end of the elongated body.

16. The steerable member of claim 1, wherein the elongated body comprises the shaft of a balloon catheter.

17. The steerable member of claim 1, wherein the elongated body comprises the shaft of an endoscope.

18. A steerable member for a medical apparatus, comprising:
  a continuously integral, elongated body having a
  b. polymer distal section, a polymer middle section, a first junction between the polymer proximal section and the polymer middle section, a second junction between the polymer middle section and the polymer proximal section, the polymer middle section extends between the first junction and the second junction;
  at least one pull wire sheath extending through the continuously integral elongated body, each of the at least one pull wire sheaths extending through the proximal section and the middle section but not extending through the distal section, wherein the middle section of the elongated body has an inner diameter smaller than the inner diameter of the proximal section, such that the pull wire sheath penetrates a wall of the elongated body where it passes into the middle section, each of the at least one pull wire sheaths heath having a channel therethrough; and
  a pull wire disposed in the channel of the sheath, the pull wire extending through the proximal section, middle section and distal section of the elongated body, the pull wire having a distal end affixed to a distal end of the elongated body;
  wherein the distal section of the elongated body bends in response to a force applied to the proximal end of the pull wire.

19. The steerable member of claim 18, wherein the sheath comprises a coil tube.

20. The steerable member of claim 19, wherein the relationship between the elastic moduli of the distal section of the elongated body and the coil tube is $$E_{polymer} \times 10^4 < E_{coil}.$$

* * * * *